United States Patent [19]

Saari et al.

[11] Patent Number: 5,227,506
[45] Date of Patent: Jul. 13, 1993

[54] ACYLOXYMETHYL ESTERS OF BISPHOSPHONIC ACIDS AS BONE RESORPTION INHIBITORS

[75] Inventors: Walfred S. Saari; Paul S. Anderson, both of Lansdale, Pa.

[73] Assignee: Merck & Co., Inc., Rahway, N.J.

[21] Appl. No.: 549,497

[22] Filed: Jul. 12, 1990

Related U.S. Application Data

[63] Continuation-in-part of Ser. No. 403,411, Sep. 6, 1989, abandoned.

[51] Int. Cl.$^5$ .............................................. C07F 9/02
[52] U.S. Cl. .................................... 514/108; 558/155; 558/156; 558/162; 558/163; 558/203; 544/337; 514/86; 514/89; 514/79; 514/90; 568/10; 546/22; 548/413; 554/78; 554/84
[58] Field of Search .............. 558/161, 162, 203, 155; 514/107, 108; 588/188, 137, 205, 177; 562/20; 509/216; 260/399, 403, 404; 568/10

[56] References Cited

U.S. PATENT DOCUMENTS

| | | | |
|---|---|---|---|
| 3,584,125 | 6/1971 | Francis et al. | 424/204 |
| 3,962,432 | 6/1976 | Schmidt-Dünker | 424/204 |
| 4,054,598 | 10/1977 | Blum et al. | 260/502.5 |
| 4,337,201 | 6/1982 | Petrillo, Jr. | 548/413 |
| 4,473,560 | 9/1984 | Biere et al. | 558/161 |
| 4,478,763 | 10/1984 | McKenna | 558/161 |
| 4,621,077 | 11/1986 | Rosini et al. | 514/108 |
| 4,719,203 | 1/1988 | Basies et al. | 588/161 |
| 4,732,998 | 3/1988 | Binderup | 558/161 |

FOREIGN PATENT DOCUMENTS

86/00902 2/1986 PCT Int'l Appl. .
87/03598 6/1987 PCT Int'l Appl. .

OTHER PUBLICATIONS

Srivastva, et al, Biorganic Chemistry, vol. 12, 1984 pp. 118-129.
Farquhar et al, Journal of Pharmaceutical Sciences, vol. 72, #3, 1983, pp. 324-325.
Chemical Abstracts, vol. 109, ∩24, p. 76, 1988 222488y.
Mortan et al., Br. J. Cancer, 58, 556-557 (1988).

*Primary Examiner*—Jose G. Dees
*Assistant Examiner*—D. D. Carr
*Attorney, Agent, or Firm*—William H. Nicholson; Robert J. North; J. Eric Thies

[57] ABSTRACT

The invention relates to acyloxymethyl esters of bisphosphonic acids, halo-bisphosphonic acids and hydroxy-bisphosphonic acids which exhibit oral bioavailability and are useful in the treatment of disturbances involving calcium or phosphate metabolism, in particular, the treatment and prevention of diseases involving bone resorption, especially osteoporosis, Paget's disease, malignant hypercalcemia, and metastatic bone disease.

21 Claims, No Drawings

ACYLOXYMETHYL ESTERS OF BISPHOSPHONIC ACIDS AS BONE RESORPTION INHIBITORS

This application is a continuation-in-part of copending application Ser. No. 403,411, filed Sep. 6, 1989, now abandoned.

The present invention relates to acyloxymethyl esters of bisphosphonic acids, halo-bisphosphonic acids and hydroxy-bisphosphonic acids, processes for their preparation, pharmaceutical compositions containing them, and methods for their use in the treatment of disturbances of calcium and phosphate metabolism, in particular, the treatment and prevention of diseases involving bone resorption, especially osteoporosis, Paget's disease, malignant hypercalcemia, and metastatic bone disease.

BACKGROUND OF THE INVENTION

The recent literature discloses a variety of hydroxybisphosphonic acids which are useful in the treatment and prevention of diseases involving bone resorption. Representative examples may be found in the following: U.S. Pat. No. 3,962,432; U.S. Pat. No. 4,054,598; U.S. Pat. No. 4,267,108; U.S. Pat. No. 4,327,039; U.S. Pat. No. 4,621,077; U.S. Pat. No. 4,746,654; and EPO Publication 0252504.

The preparation of bisphosphonic acids and halo-bisphosphonic acids is also well known in the art. Representative examples may be found in the above mentioned references which dislose the compounds as being useful for the treatment of disturbances of calcium or phosphate metabolism, in particular, as inhibitors of bone resorption.

The bisphosphonic acids mentioned in the above references suffer from the problem of low oral bioavailability and, in addition, may exhibit gastrointestinal side effects particularly with the large oral doses required to provide therapeutic efficacy (see *Br. J. Cancer*, 52, 556 (1988)).

The preparation of simple esters of bisphosphonic acids and hydroxy-bisphosphonic acids, such as methyl, ethyl, propyl, and the like, is known in the art (for example see U.S. Pat. No. 3,705,191, U.S. Pat. No. 4,309,364, U.S. Pat. No. 4,371,527, U.S. Pat. No. 4,732,998, U.S. Pat. No. 4,746,654, EPO Publication 0252504, and *J. Med. Chem.*, 30, 1426, (1987)). However, these simple esters are not readily hydrolyzed in vivo and do not yield satisfactory blood levels of the corresponding bisphosphonic acids.

Acyloxymethyl esters of monophosphates and monophosphinates have been reported (see U.S. Pat. No. 4,337,201, *Bioorganic Chem.*, 1984, 12, 118, *J. Pharm. Sci.*, 1983, 72, 324). Also, U.S. Pat. No. 4,732,998, U.S. Pat. No. 4,870,063, and PCT Publication No. WO 86/00902 describe alkanoyloxymethyl esters of thiomorpholino, alkoxy and aryloxy substituted bisphosphonic acids. However, the preparation of acyloxymethyl esters of the more potent hydroxy-bisphosphonic acids has not been previously described. Nor has the art recognized that these compounds may overcome the problem of poor oral bioavailability associated with the hydroxy-bisphosphonic acids of the prior art.

SUMMARY OF THE INVENTION

This invention relates to compounds of the general formula I:

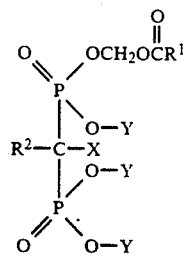

or a pharmaceutically acceptable salt thereof, wherein:
$R^1$ is independently, $C_{1-12}$alkyl;
$R^2$ is
1) $C_{1-10}$alkyl, either unsubstituted or substituted with
   a) $-NR^3R^4$, wherein R3 and R4 are the same or different and are
      i) hydrogen,
      ii) $C_{1-6}$alkyl, or
      iii) joined together directly to form a 5-7 membered ring selected from pyrrolidino, and piperidino or through a heteroatom selected from O and N, to form a 6-membered heterocycle selected from morpholino, piperazino, and N-$C_{1-3}$alkyl-piperazino with the nitrogen to which they are attached.
   b) $-OH$
   c) halo,
   d) $-S(C_{1-6}$alkyl),
   e) phenyl,
   f) $C_{1-7}$cycloalkyl, either unsubstituted or substituted with
      i) $-NR^3R^4$,
      ii) $-OH$, or
   g) pyridyl;
2) $C_{3-7}$cycloalkyl, either unsubstituted or substituted with
   a) $-NR^3R^4$,
   b) $-OH$,
   c) halo,
   d) $-S(C_{1-6}$alkyl),
   e) phenyl,
   f) morpholino, or
   g) pyridyl;
3) halo;
4) piperidinyl;
5) pyrrolidinyl;
6) $-S-(C_{1-6}$alkyl), either unsubstituted or substituted with
   a) $-NR^3R^4$,
   b) $-OH$,
   c) halo, or
   d) phenyl,
7) $-S-$phenyl wherein the phenyl may be unsubstituted or substituted with
   a) halo,
   b) nitro,
   c) $C_{1-6}$alkyl,
   d) $C_1$-$C_6$ alkoxy,
   e) trifluoromethyl,
   f) $-CONR^3R^4$, or
   g) $-COOH$;
Y is independently, hydrogen or

wherein $R^1$ is as defined above; and

X is hydrogen, halo or hydroxyl.

In the present invention the compounds may have asymmetric centers and occur as racemates, racemic mixtures and as individual diastereomers, with all isomeric forms being included in the present invention.

When any variable (e.g. alkyl, $R^1$, Y etc.) occurs more than one time in any constituent of formula I, its definition on each occurrence is independent of its definition at every other occurrence. Also, combinations of substituents and/or variables are permissible when such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl, etc.); "alkoxy" represents an alkyl group of indicated number of carbon atoms attached through an oxygen bridge; "cycloalkyl" is intended to include saturated ring groups, such cyclopropyl, cyclobutyl, cyclopentyl, cyclohexyl and cycloheptyl; and "alkylcycloalkyl" is intended to include saturated ring groups, such cyclopropyl, cyclobutyl, cyclopentyl, cyclohexyl and cycloheptyl which are attached to a branched- or a straight-chain saturated aliphatic hydrocarbon group. "Alkanoyl" is intended to include those alkylcarbonyl groups of specified number of carbon atoms, which are exemplified by formyl, acetyl, propanoyl, butanoyl, etc.; "alkenyl" is intended to include hydrocarbon chains of either a straight- or branched- configuration and one or more unsaturated carbon-carbon bonds which may occur at any stable point along the chain, such as ethenyl, propenyl, butenyl, pentenyl, and the like. "Halo", as used herein, means fluoro, chloro, bromo and iodo.

One embodiment of the compounds of the present invention encompasses those compounds in which X is hydroxyl. In this embodiment, it is preferred that:

$R^1$ is independently, $C_1$-$C_{12}$ alkyl;

$R^2$ is
1) $C_{1-6}$alkyl, either unsubstituted or substituted with
   a) $-NR^3R^4$, wherein R3 and R4 are the same or different and are
      i) hydrogen,
      ii) $C_{1-6}$alkyl, or
      iii) joined together directly to form a 5–7 membered ring selected from pyrrolidino, and piperidino or through a heteroatom selected from O and N, to form a 6-membered heterocycle selected from morpholino, piperazino, and N-$C_{1-3}$alkyl-piperazino with the nitrogen to which they are attached,
   b) pyridyl;
2) piperidinyl; or
3) pyrrolidinyl.

In this embodiment, it is even more preferred that:

$R^1$ is tert-butyl, isobutyl, 2-ethylbutyl or 2,2-dimethylbutyl;

$R^2$ is $C_1$-$C_4$ alkyl either unsubstituted or substituted with
   a) amino,
   b) N,N-dimethylamino,
   c) N-methyl-N-pentylamino, or
   d) N-methyl-N-isobutylamino.

A second embodiment of the compounds of the present invention encompasses those compounds in which X is chloro. In this embodiment, it is preferred that:

$R^1$ is independently $C_1$-$C_{12}$ alkyl; and $R^2$ is halo.

In this embodiment, it is even more preferred that:

$R^1$ is tert-butyl, isobutyl, 2-ethylbutyl or 2,2-dimethylbutyl; and $R^2$ is chloro.

A third embodiment of the compounds of the present invention encompasses those compounds in which X is fluoro. In this embodiment, it is preferred that:

$R^1$ is independently $C_1$-$C_{12}$ alkyl; and $R^2$ is halo.

In this embodiment, it is even more preferred that:

$R^1$ is tert-butyl, isobutyl, 2-ethylbutyl or 2,2-dimethylbutyl; and $R^2$ is fluoro.

Preferred compounds of the present invention are the compounds identified as follows:

4-amino-1-hydroxybutylidene-1,1-bisphosphonic acid mono(pivaloyloxymethyl) ester;

4-amino-1-hydroxybutylidene-1,1-bisphosphonic acid di(pivaloyloxymethyl) ester;

4-amino-1-hydroxybutylidene-1,1-bisphosphonic acid tri(pivaloyloxymethyl) ester;

4-amino-1-hydroxybutylidene-1,1-bisphosphonic acid tetra(pivaloyloxymethyl) ester;

4-amino-1-hydroxybutylidene-1,1-bisphosphonic acid di(pivaloyloxymethyl) ester monosodium salt;

4-amino-1-hydroxybutylidene-1,1-bisphosphonic acid di[(2-ethyl)butanoyloxymethyl] ester;

4-amino-1-hydroxybutylidene-1,1-bisphosphonic acid tri[(2-ethyl)butanoyloxymethyl] ester;

4-amino-1-hydroxybutylidene-1,1-bisphosphonic acid tri(2,2-dimethylbutanoyloxymethyl) ester;

4-amino-1-hydroxybutylidene-1,1-bisphosphonic acid tri(isobutanoyloxymethyl) ester;

N-methyl-4-amino-1-hydroxybutylidene-1,1-bisphosphonic acid di(pivaloyloxymethyl) ester;

N-methyl-4-amino-1-hydroxybutylidene-1,1-bisphosphonic acid tri(pivaloyloxymethyl) ester;

N-methyl-4-amino-1-hydroxybutylidene-1,1-bisphosphonic acid di[(2-ethyl)butanoyloxymethyl] ester;

N-methyl-4-amino-1-hydroxybutylidene-1,1-bisphosphonic acid tri[(2-ethyl)butanoyloxymethyl] ester;

4-(N,N-dimethylamino)-1-hydroxybutylidene-1,1-bisphosphonic acid tri(pivaloyloxymethyl) ester;

3-amino-1-hydroxypropylidene-1,1-bisphosphonic acid tri(pivaloyloxymethyl) ester;

3-(N,N-dimethylamino)-1-hydroxypropylidene-1,1-bisphosphonic acid tri(pivaloyloxymethyl) ester;

1-hydroxy-3-(N-methyl-N-pentylamino)propylidene-1,1-bisphosphonic acid tri(pivaloyloxymethyl) ester;

1-hydroxyethylidene-1,1-bisphosphonic acid tri(pivaloyloxymethyl) ester;

[(4-chlorophenyl)thio]methylene-1,1-bisphosphonic acid tri(pivaloyloxymethyl) ester;

1-hydroxy-2-[3-pyridyl]ethylidene-1,1-bisphosphonic acid tri(pivaloyloxymethyl) ester;

4-(hydroxymethylene-1,1-bisphosphonic acid)piperidine tri(pivaloyloxymethyl) ester;

dichloromethylene-1,1-bisphosphonic acid tetra(pivaloyloxymethyl) ester; and difluoromethylene-1,1-bisphosphonic acid tetra(pivaloyloxymethyl) ester.

The pharmaceutically acceptable salts of the compounds of formula I include the conventional non-toxic salts or the quaternary ammonium salts of these compounds, which are formed, e.g., from inorganic or organic acids or bases and also internal, i.e. zwitterionic, salts. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, pivalate, propionate, succinate, tartrate, thiocyanate, tosylate, and undecanoate. Base salts include ammonium salts, alkali metal salts such as potassium and sodium (including mono-, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. The non-toxic, physiologically acceptable salts are preferred, although other salts are also useful, e.g. in isolating or purifying the product. The salts may be prepared by methods known in the art.

In addition, the invention also relates to a process for the production of the above acyloxymethyl esters of bisphosphonic acids, halo-bisphosphonic acids and hydroxy-bisphosphonic acids comprising the reaction of a bisphosphonic acid, halo-bisphosphonic acid or hydroxy-bisphosphonic acid (suitably protected when necessary) with an appropriate halomethyl ester in the presence of a suitable base in an organic solvent such as N,N-dimethylformamide followed by removal of the protecting group (if present) under conditions suitable for its removal.

More particularly, this invention relates to the preparation of acyloxymethyl esters of bisphosphonic acids, halo-bisphosphonic acid and hydroxy-bisphosphonic acids which exhibit oral bioavailability and which have utility in the treatment of disturbances involving calcium or phosphate metobolism, in particular, the treatment of and prevention of diseases involving bone resorption, especially osteoporosis, Paget's disease, malignant hypercalcemia, and metastatic bone disease.

PREPARATION OF THE COMPOUNDS OF THE PRESENT INVENTION

The starting materials for the preparation of the compounds of this invention are represented by formula II:

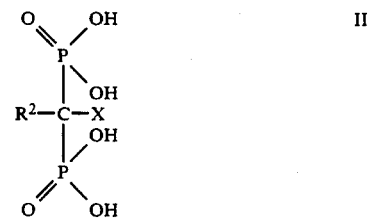

wherein $R^2$ and X are as defined above.

The production of hydroxy-bisphosphonic acids of formula II is well known in the literature. Representative examples may be found in the following: U.S. Pat. Nos. 3,251,907; 3,422,137; 3,584,125; 3,940,436; 3,944,599; 4,054,598; 4,267,108; 4,327,039; 4,621,077; 4,746,654; EPO Publication 0252504; *J. Org. Chem.*, 1971, 36, 3843.

The production of bisphosphonic acids and halo-bisphosphonic acids of formula II is also well known in the art literature. Representative examples may be found in the the above mentioned references.

The compounds of the present invention which are represented by formula I are prepared by the methods shown in the following Reaction Scheme wherein PG is a suitable protective group, Z is chloro, bromo or iodo and $R^1$, $R^2$, X and Y are as defined above unless otherwise indicated. It will be readily apparent to one of ordinary skill in the art reviewing the synthetic route depicted below that other compounds within formula I can be synthesized by substitution of appropriate reactants and agents in the synthesis shown below.

REACTION SCHEME

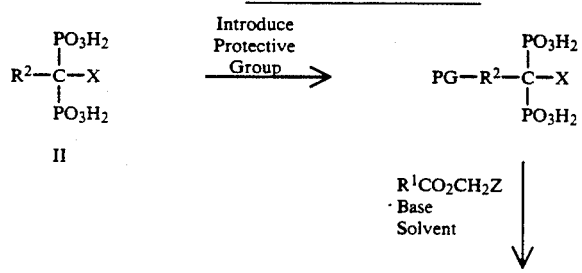

REACTION SCHEME -continued

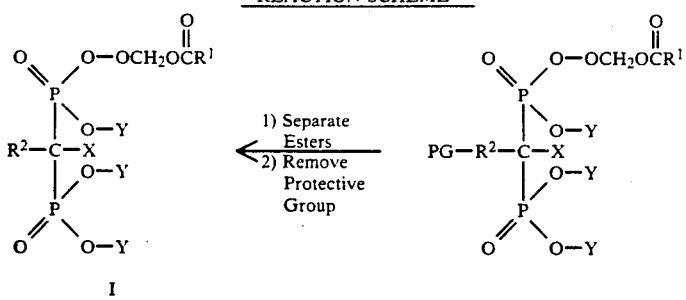

In general, a bisphosphonic acid, halo-bisphosphonic acid or hydroxy-bisphosphonic acid, II, is protected with an amino-protecting group if a free amino group is present, such as by reaction with benzylchloroformate in a solution of water and a miscible organic solvent, such as acetonitrile or tetrahydrofuran, in the presence of an inorganic hydroxide base, such as NaOH.

The bisphosphonic acid, halo-bisphosphonic acid or hydroxy-bisphosphonic acid (bearing an amino-protecting group if necessary) is reacted with an appropriate halomethyl ester (such as chloromethyl pivalate, chloromethyl (2-ethyl)butyrate, chloromethyl (2,2-dimethyl)butyrate, iodomethyl isobutyrate, and the like) in the presence of a suitable amine base (such as diisopropylethylamine, triethylamine, and the like), optionally in the presence of a quarternary ammonium salt (such as tetrabutylammonium iodide, tetrabutylammonium bromide, tetramethylammonium iodide, and the like), in an organic solvent (such as dimethylformamide, and the like) at a temperature of about 20° C. to 80° C. for a period of 2 hours to 4 days to give a mixture of the mono-, di-, tri- and tetra(acyloxymethyl) esters of the bisphosphonic acid, halo-bisphosphonic acid or hydroxy-bisphosphonic acid which can be separated by conventional methods.

The protecting group, if present, is removed under conditions suitable for its removal. For example, the amino-protecting group benzyloxycarbonyl (CBZ), if present, may be removed by hydrogenolysis under an atmosphere of hydrogen in the presence of a noble metal catalyst such as palladium on carbon catalyst or palladium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to fully cleave the CBZ protecting group. The resultant deprotected bisphosphonate, halo-bisphosphonate or hydroxy-bisphosphonate, I, is isolated by conventional methods, such as crystallization, lyophilization, or chromatography. When no protecting group is required the reactions involving introduction and removal of a protecting group may be omitted.

For hydroxy-bisphosphonic acids containing a basic nitrogen suitable amino-protecting groups include the benzyl, benzyloxymethyl, benzyloxycarbonyl (carbobenzyloxy), benzylsulfonyl, 2-bromoethyloxycarbonyl, t-butyloxycarbonyl, 2-chlorobenzyloxycarbonyl, 2-chloroethyloxycarbonyl, 9-fluorenylmethyloxycarbonyl, isopropoxycarbonyl, 4-methoxybenzyloxycarbonyl, 4-nitrobenzyloxycarbonyl, 2-nitrophenylsulfonyl, phthaloyl, 2,2,2-trichloro-t-butyloxycarbonyl, trifluoroacetyl, triphenylmethane and vinyloxycarbonyl groups, and the like which are known in the art, in which the preferred ones are the t-butyloxycarbonyl, benzyloxycarbonyl (carbobenzyloxy), 2-chlorobenzyloxycarbonyl, 4-methoxybenzyloxycarbonyl and 4-nitrobenzyloxycarbonyl groups and in which the more preferred ones are the t-butyloxycarbonyl and the benzyloxycarbonyl (carbobenzyloxy) groups.

UTILITY OF THE COMPOUNDS OF THE PRESENT INVENTION

The compounds of formula I are useful in the therapeutic or prophylactic treatment of disorders in calcium or phosphate metabolism and associated diseases. These diseases can be divided into two categories:

1. Abnormal (ectopic) depositions of calcium salts, mostly calcium phosphate, pathological hardening of tissues and bone malformations.

2. Conditions which can benefit from a reduction in bone resorption. A reduction in bone resorption should improve the balance between resorption and formation, reduce bone loss or result in bone augmentation. A reduction in bone resorption can aleviate the pain associated with osteolytic lesions and reduce the incidence and/or growth of those lesions.

These diseases include: osteoporosis (including estrogen defficiency, immobilization, glucocorticoid induced and senile), osteodystrophy, Paget's disease, myositis ossificans, Bechterew's disease, malignant hypercalcimia, metastatic bone disease, peridontal disease, cholelithiasis, nephrolithiasis, urolithiasis, urinary calculus, hardening of the arteries (sclerosis), arthritis, bursitis, neuritis and tetany.

Increased bone resorption can be accompanied by pathologically high calcium and phosphate concentrations in the plasma, which would be aleviated by this treatment.

For treatment of these conditions and diseases, it is possible to apply the compounds of the invention to a human (in suitable dosage unit formulations containing conventional non-toxic pharmaceutically acceptable carriers, adjuvants and vehicles) by oral, rectal, parenteral (including subcutaneous injections, intravenous, intramuscular, intrasternal injection or infusion techniques) or topical administration, however, it is preferable to apply them by oral administration.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient suitable for oral administration may be in the form of discrete units such as hard or soft capsules, tablets, troches or lozenges, each containing a predetermined amount of the active ingredient; in the form of a dispersible powder or granules; in the form of a solution or a suspension in an aqueous liquid or non-aqueous liquid; in the form of syrups or elixirs; or in the form of an oil-in-water emulsion or a water-in-oil emulsion. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintergrating agents such as corn starch, or alginic acid; (3) binding agents such as starch, gelatin or acacia; and (4) lubricating agents such as magnesium stearate, stearic acid or talc. The tablets may be uncoated or they may be coated by known techniques to delay disintegration and absorption in the gastroinestinal tract and thereby provide a sustained action over a longer period. For example, a time delay material such as glyceryl monostearate or glyceryl disearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodum carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occuring phosphatide such as lecithin,
  (b) a condensation product of an alkylene oxide with a fatty acid, for example, polyoxyethylene sterate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occuring gums such as gum acacia and gum tragacanth, (2) naturally-occuring phosphatides such as soy bean and lecithin, (3) esters or partial esters derived from fatty acids and hexitol anhydrides, for example, sorbitan monooleate, (4) condensation products of said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension or solution. The suspension may be formulated according to known methods using those suitable dispersing or wetting agents and suspending agents which have been mentioned above. The sterile injectable preparation may also be a sterile injectable solution or suspension in a non-toxic paternterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical administration the compounds of this invention may be formulated in liquid or semi-liquid preparations such as liniments, lotions, applications; oil-in-water or water-in-oil emulsions such as creams, ointments, jellies or pastes, including tooth-pastes; or solutions or suspensions such as drops, and the like.

The pharmaceutical compositions may further contain other therapeutically active compounds usually applied in the treatment of the above mentioned pathological conditions, for instance vitamin $D_2$ and $D_3$ and hydroxylated derivatives, e.g. $1\alpha$-hydroxy-vitamin $D_3$, $1\alpha$-hydroxy-vitamin $D_2$, $1\alpha,25$-dihydroxy-vitamin $D_3$, $1\alpha,25$-dihydroxy-vitamin $D_2$, calcitonin (human, porcine or salmon), mitramycin, sodium fluoride, estrogens, and non-steroid antiinflammatory drugs, e.g. acetylsalicyclic acid, indomethacin, naprosyn, and timegadine.

The magnitude of a prophylactic or therapeutic dose of a compound or compounds of formula I will, of course, vary with the age and the nature or the severity of the condition of each individual patient to be treated and with the particular compound or compounds of formula I and its route of administration. In general, the daily oral dose for bone resorption disease use lies within the range of from about 0.5 μg to about 1 mg per kg body weight and, preferably, within the range of from 1 μg to 800 μg per kg body weight and can be administered in up to four doses daily. For prophylaxis of diseases involving bone resorption such as postmenopausal osteoporosis, the daily oral dose lies within the range of from about 5 μg to 200 μg per kg body weight and, preferably, within the range of from 20 μg to 100 μg per kg body weight. The daily parenteral dose for bone resorption disease use lies within the range of from about 50 μg to about 3 mg per kg body weight and, preferably, within the range of from 200 μg to 1.5 mg per kg body weight.

A compound or compounds of formula I may also be administered on an intermittent basis. For the treatment or prophylaxis of diseases involving bone resorption a typical primary oral dose which lies within the range of from about 10 μg to 10 mg per kg body weight may be administered and then, if necessary a sustaining dose approximately equal to half of the primary dose may be administered at weekly, semiweekly, semimonthly, monthly, bimonthly, quarterly, semiannual, annual or biannual intervals.

The following examples are given for the purpose of illustrating the present invention and shall not be construed as being limitations on the scope or spirit of the instant invention.

EXAMPLE 1

Protection of amino hydroxy-bisphosphonic acids

A. Preparation of 4-Benzyloxycarbonylamino-1-hydroxybutylidene-1,1-bisphosphonic Acid Aqueous NaOH solution, 1.0N (3.1 ml, 3.1 mmol) was added to a stirred solution of 4-amino-1-hydroxybutylidene-1,1-bisphosphonic acid disodium salt monohydrate (1.00 g, 3.2 mmol) in 40% THF-water (37 ml). After 5 minutes, the pH stabilized at 9.0 and benzylchloroformate (0.6 ml, 4.2 mmol) was added dropwise over 5 minutes. During the addition, pH was maintained at 8.6–9.0 by the addition of 1.0N NaOH as needed. The mixture was then stirred at room temperature for 18 hours, pH was adjusted to 9.0 and most of the THF was removed under reduced pressure. Absolute EtOH was added to the remaining aqueous solution to precipitate the sodium salt of 4-benzyloxycarbonylamino-1-hydroxybutylidene-1,1-bisphosphonic acid.

A solution of this sodium salt in water was passed through a column of Dowex 50X4-400 ion exchange resin in the acid form and the column eluted with water. The strongly acidic fractions were combined and lyophilized to give 0.80 g (66%) of 4-benzyloxycarbonylamino-1-hydroxybutylidene-1,1-bisphosphonic acid.

Anal. Calcd. for $C_{12}H_{19}NO_9P_2 \cdot 0.5H_2O$: C, 36.74; H, 5.14; N, 3.57; Found: C, 36.82; H, 5.05; N, 3.50.

B. Preparation of 4-Benzyloxy-carbonylamino-1-hydroxybutylidene-1,1-bisphosphonic Acid (Alternate Method)

4-Amino-1-hydroxybutylidene-1,1-bisphosphonic acid monosodium salt trihydrate (25 g, 0.077 mol) was suspended in 170 ml of deionized water with stirring. Sodium hydroxide (5.0N) was added dropwise until a pH of 9.0 was achieved, resulting in a clear solution. Acetonitrile (55 ml) was added to the solution, followed by benzyl chloroformate (13 ml, 0.091 mol) in one portion. Additional sodium hydroxide (5.0N) was added at such a rate so as to maintain a pH 8.5–9.0 as the solution was aged at room temperature for 2 hours. The reaction was extracted with 150 ml of tert-butyl methyl ether and the aqueous portion was concentrated under reduced pressure to remove the residual ether.

The product was isolated by one of the following methods (method A is the preferred method of isolation).

(A) The solution was passed over a Dowex (50X4) ion exchange column in the acid form and eluted with water. The most acidic portions of the column eluate (pH <3.5) were collected and concentrated under reduced pressure to a thick syrup. Dimethylformamide was added and the mixture was concentrated several times to azeotropically remove residual water. The dimethylformamide solution was assayed for product and used without purification.

(B) The solution was chromatographed as in method A and the column eluent was lyophilized. The yield was 25.9–27.9 grams (88–95%) of product.

Anal. Calcd. for $C_{12}H_{19}NO_9P_2 \cdot 2H_2O$: C, 32.65; H, 5.22; N, 3.17; Found: C, 33.40; H, 4.91; N, 3.38.

$^{31}P$-NMR($D_2O$)($H_3PO_4$ reference): δ 19.0 (s).

(C) The monosodium salt was isolated in 80–90% yield by adjusting the pH of the solution to 1.8 with hydrochloric acid, adding five volumes of ethanol, and aging for 3 hours. The monosodium salt was collected by filtration.

All glassware used in Example 1B was soaked in dilute nitric acid and rinsed throughly with water prior to use.

C. Preparation of N-methyl-4-benzyloxycarbonylamino-1-hydroxybutylidene-1,1-bisphosphonic Acid N-Methyl-4-amino-1-hydoxy-butylidene-1,1-bisphosphonic acid monosodium salt (5 g, 0.015 mol) was reacted under procedures described in Example 1B to yield 4.1 g (71% yield) of the title compound.

D. Preparation of 3-Benzyloxycarbonylamino-1-hydroxypropylidene-1,1-bisphosphonic Acid Following the procedure of Example 1A or 1B the title compound is prepared by treatment of a solution of 3-amino-1-hydroxypropylidene-1,1-bisphosphonic acid in THF-water with an aqueous solution of NaOH followed by addition of benzylchloroformate and isolation of the product as described.

E. Preparation of N-Benzyloxycarbonyl-4-(1-hydroxymethylene-1,1-bisphosphonic acid)piperidine Following the procedure of Example 1A or 1B the title compound is prepared by treatment of a solution of 4-(1-hydroxymethylene-1,1-bisphosphonic acid)-piperidine in THF-water with an aqueous solution of NaOH followed by addition of benzylchloroformate and isolation of the product as described.

EXAMPLE 2

Esterification of bisphosphonic acids

A. Preparation of 4-Benzyloxycarbonylamino-1-hydroxybutylidene-1,1-bisphosphonic Acid Tri(pivaloxyloxymethyl) Ester and 4-Benzyloxycarbonylamino-1-hydroxybutylidene-1,1-bisphosphonic Acid Di(pivaloyloxymethyl) Ester A solution of 4-benzyloxycarbonylamino-1-hydroxybutylidene-1,1-bisphosphonic acid hemihydrate (1.0 g, 2.55 mmol), diisopropylethylamine (1.8 ml, 10.2 mmol) and chloromethylpivalate (1.54 g, 10.2 mmol) in N,N-dimethylformamide (DMF) (50 ml) was stirred at 60° C. for 4 hours. After concentrating at 50° C. and 0.1 mm, the residue was partitioned between EtOAc and water. The organic extract was washed with brine, dried ($Na_2SO_4$), filtered and concentrated to a gum. Preparative HPLC purification over a C-18 reverse phase column and elution with $H_2O-CH_3CN$ gradient (0–60% over 60 min.) afforded >90% pure samples of 4-benzyloxycarbonylamino-1-hydroxybutylidene-1,1-bisphosphonic acid tri(pivaloyloxymethyl) ester and 4-benzyloxycarbonylamino-1-hydroxybutylidene-1,1-bisphosphonic acid di(pivaloyloxymethyl) ester.

B. Preparation of 4-Benzyloxy-carbonylamino-1-hydroxybutylidene-1,1-bisphosphonic Acid Tri(pivaloxymethyl) Ester (Alternate method)

Under an atmosphere of nitrogen 16 ml (0.113 mol) of chloromethyl pivalate, 14.4 g (0.038 mol) of tetrabutylammonium iodide, and 15 ml (0.085 mol) of diisopropylethylamine were added to 7.2 g (0.019 mol) of 4-benzyloxycarbonylamino-1-hydroxybutylidene-1,1-bisphosonic acid in 36 ml of N,N-dimethylformamide. The reaction mixture was aged at room temperature for 2-3 days.

The reaction was concentrated under reduced pressure at 35°–40° C. The solution was flushed with an additional 45 ml of dimethylformamide and reconcentrated. An equal volume (250 ml) of deionized water and tert-butyl methyl ether or isopropyl acetate was added to the resulting oil and the layers were partitioned. The organic phase was washed with the following: twice with 100 ml of 2.5% sodium bisulfite, twice with 100 ml of 2.5% sodium bicarbonate, twice with 100 ml of 2% HCl, and twice with 50 ml deionized water. The organic phase was concentrated under reduced pressure at 25° C., resulting in a viscous oil which contained 5.9 g of the title compound.

All glassware used in Example 2B was soaked in dilute nitric acid and rinsed thoroughly with water prior to use.

C. Preparation of 4-Benzyloxycarbonylamino-1-hydroxybutylidene-1,1-bisphosphonic Acid Di(pivaloyloxymethyl) Ester monosodium salt Following the procedure of Example 2B, 4-benzyloxycarbonylamino-1-hydroxybutylidene-1,1-bisphosphonic acid di(pivaloyloxymethyl) ester was prepared, beginning with 4.2 g (0.01 mol) of 4-benzyloxycarbonylamino-1-hydroxybutylidene-1,1-bisphosphonic acid. All aqueous washes were combined, acidified to pH 2 with hydrochloric acid, and extracted with 250 ml of isopropyl acetate. The organic extract was washed with 200 ml of saturated sodium chloride solution and then aged at −18° C. for several days, during which time the sodium salt of the diester crystallized. The salt was collected by filtration and dried, giving 2 grams (30% yield) of the title compound.

All glassware used in Example 2C was soaked in dilute nitric acid and rinsed thoroughly with water prior to use.

Anal. Calcd. for $C_{24}H_{39}NO_{11}P_2$; C, 45.50; H, 6.16; N, 2.21; Found: C, 44.80; H, 6.26; N, 2.11. (Corrected for Karl-Fisher (4.28%) and NaCl (3.07%)).

$^{31}P$-NMR ($CD_3OD$)($H_3PO_4$ reference): δ 15.9 (s).

D. Preparation of 4-Benzyloxycarbonylamino-1-hydroxybutylidene-1,1-bisphosphonic Acid Tri[(2-ethyl)butanoyloxymethyl] Ester Following the procedure of Example 2B, 4-benzyloxycarbonylamino-1-hydroxybutylidene-1,1-bisphosphonic acid (2 g, 0.005 mol) was alkylated with chloromethyl (2-ethyl)butyrate (prepared as described in J. Am. Chem. Soc., 1967, 89 (21), 5439–5440 and used without distillation) as described in Example 2B to give 974 mg of the title compound.

E. Preparation of 4-Benzyloxycarbonylamino-1-hydroxybutylidene-1,1-bisphosphonic Acid Di[(2-ethyl)butanoyloxymethyl] Ester Following the procedure of Example 2B, 4-benzyloxycarbonylamino-1-hydroxybutylidene-1,1-bisphosphonic acid (2 g, 0.005 mol) was alkylated with chloromethyl (2-ethyl)butyrate (prepared as described in J. Am. Chem. Soc., 1967, 89 (21), 5439–5440 and used without distillation) as described in Example 2B to give the title compound.

F. Preparation of N-Methyl-4-benzyloxycarbonylamino-1-hydroxybutylidene-1,1-bisphosphonic Acid Tri(pivaloyloxymethyl) Ester N-Methyl-4-benzyloxycarbonylamino-1-hydroxybutylidene-1,1-bisphosphonic acid (1.75 g, 0.004 mol) was reacted with chloromethyl pivalate under the procedure described in Example 2B to give 600 mg of the title compound.

G. Preparation of N-Methyl-4-benzyloxycarbonylamino-1-hydroxybutylidene-1,1-bisphosphonic Acid Di(pivaloyloxymethyl) Ester N-Methyl-4-benzyloxycarbonylamino-1-hydroxybutylidene-1,1-bisphosphonic acid (1.75 g, 0.004 mol) was reacted with chloromethyl pivalate under the procedure described in Example 2B to give 190 mg of the title compound.

H. Preparation of N-Methyl-4-benzyloxycarbonylamino-1-hydroxybutylidene-1,1-bisphosphonic Acid Tri[(2-ethyl)butanoyloxymethyl] Ester N-Methyl-4-benzyloxycarbonylamino-1-hydroxybutylidene-1,1-bisphosphonic acid (1.75 g, 0.004 mol) was reacted with chloromethyl (2-ethyl)butyrate under the procedure described in Example 2B to give of the title compound.

I. Preparation of N-methyl-4-benzyloxycarbonylamino-1-hydroxybutylidene-1,1-bisphosphonic Acid Di[(2-ethyl)butanoyloxymethyl] Ester N-Methyl-4-benzyloxycarbonylamino-1-hydroxybutylidene-1,1-bisphosphonic acid (1.75 g, 0.004 mol) was reacted with chloromethyl (2-ethyl)butyrate under the procedure described in Example 2C. The title compound was not crystallized, but was extracted into isopropyl acetate. The organic phase was concentrated and the product was utilized without further purification.

J. Preparation of N,N-Dimethyl-4-amino-1-hydroxybutylidene-1,1-bisphosphonic Acid Tri(pivaloyloxymethyl) Ester 4-Amino-1-hydroxybutylidene-1,1-bisphosphonic acid tri(pivaloyloxymethyl) ester (0.5 g, 0.0008 moles) was dissolved in 10 ml methanol and hydrogenated over 125 mg of 5% Pd on carbon in the presence of 5 ml (0.063 moles) of aqueous formaldehyde at 40 psi and 25° C. for 90 minutes. The catalyst was removed by filtration and washed with methanol. Methanol was removed under reduced pressure and the residue was dissolved in dry isopropyl acetate. Water was added and the product crystallized to provide 200 mg (40% yield) of the title compound.

Anal. Calcd. for $C_{24}H_{47}NO_{13}P_2$: C,46.52; H, 7.59; N, 2.26; Found: C, 46.44; H, 7.71; N, 2.20;

$^{31}$P-NMR($CD_3OD$)($H_3PO_4$ reference): δ10.0–10.4 (d, J=35 Hz), 21.3–21.6 (d, J=35 Hz).

K. Preparation of N,N-Dimethyl-4-amino-1-hydroxybutylidene-1,1-bisphosphonic Acid Di(pivaloyloxymethyl) Ester 4-Amino-1-hydroxybutylidene-1,1-bisphosphonic acid tri(pivaloyloxymethyl) ester monosodium salt (0.5 g, 0.001 mol) was hydrogenated under the procedure of Example 2J to give 200 mg (38% yield) of the title compound.

Anal. Calcd. for $C_{18}H_{37}NO_{11}P_2$: C, 40.99; H, 6.83; N, 2.66; Found: C, 40.77; H, 6.74; N, 2.61; (Corrected for KarlFisher (5.41%) and NaCl (4.16%).

$^{31}$P-NMR($CD_3OD$)($H_3PO_4$ reference): δ 15.7 (s).

L. Preparation of 4-Benzyloxycarbonylamino-1-hydroxybutylidene-1,1-bisphosphonic Acid Tri(isobutanoyloxymethyl) Ester Substitution of iodomethylisobutyrate for chloromethylpivalate and reaction with 4-benzyloxycarbonylamino-1-hydroxybutylidene-1,1-bisphosphonic acid hemihydrate and diisopropylethylamine in DMF and isolation as described in Example 2A gives the title compound.

M. Preparation of 3-Benzyloxycarbonylamino-1-hydroxypropylidene-1,1-bisphosphonic Acid Tri(pivaloyloxymethyl) Ester Following the procedure of Example 2A the title compound is prepared by the reaction of a solution of 3-benzyloxycarbonylamino-1-hydroxypropylidene-1,1-bisphosphonic acid and chloromethylpivalate in DMF in the presence of diisopropylethylamine followed by isolation as described.

N. Preparation of N-Benzyloxycarbonyl-4-(1-hydroxymethylene-1,1-bisphosphonic acid)piperidine Tri(pivaloyloxymethyl) Ester Following the procedure of Example 2A the title compound is prepared by the reaction of a solution of N-benzyloxycarbonyl-4-(1-hydroxymethylene-1,1-bisphosphonic acid)piperidine and chloromethylpivalate in DMF in the presence of diisopropylethylamine followed by isolation as described.

O. Preparation of 3-(N,N-Dimethylamino)-1-hydroxypropylidene-1,1-bisphosphonic Acid Tri(pivaloyloxymethyl) Ester A solution of 3-(N,N-dimethylamino)-1-hydroxypropylidine-1,1-bisphosphonic acid (1.5 g, 5.7 mmol), triethylamine (2.6 ml, 18.8 mmol), and chloromethylpivalate (2.7 ml, 18.8 mmol) in DMF (75 ml) is stirred at 60° C. for 4 hours. After concentrating at 50° C. and 0.1 mm, the residue is purified by preparative HPLC with a $H_2O$-$CH_3CN$ gradient (0–60% over 60 minutes) to give the tri(pivaloyloxymethyl) ester of 3-(N,N-dimethylamino-1-hydroxy-propylidene-1,1-bisphosphonic acid.

P. Preparation of 3-(N-Methyl-N-pentylamino)-1-hydroxypropylidene-1,1-bisphosphonic Acid Tri(pivaloyloxymethyl) Ester Substitution of 3-(N-methyl-N-pentylamino)-1-hydroxypropylidene-1,1-bisphosphonic acid for 3-(N,N-dimethylamino)-1-hydroxypropylidene-1,1-bisphosphonic acid in Example 2F gives the tri(pivaloyloxymethyl) ester of 3-(N-methyl-N-pentylamino)-1-hydroxypropylidene-1,1-bisphosphonic acid.

Q. Preparation of 1-Hydroxy-2-[3-pyridyl] ethylidine-1,1-bisphosphonic Acid Tri(pivaloyloxymethyl) Ester Substitution of 1-hydroxy-2-[3-pyridyl] ethylidine-1,1-bisphosphonic acid for 3-(N,N-dimethylamino)-1-hydroxypropylidine -1,1-bisphosphonic acid of Example 2F gave the tri(pivaloyloxymethyl) ester of 1-hydroxy-2-[3-pyridyl]ethylidene-1,1-bisphosphonic acid. In this Example, 0.15% trifluoroacetic acid:$CH_3CN$ was used as the gradient for the preparative HPLC.

Anal. Calcd, For $C_{19}H_{31}NO_{11}P_2.0.75CF_3CO_2H$: C, 41.25; H, 5.36; N, 2.35; Found: C, 41.62; H, 5.25; N, 1.87.

R. Preparation of 1-Hydroxyethylidene-1,1-bis-phosphonic Acid Tetra(pivaloyloxymethyl) Ester Reaction of a solution of 1-hydroxyethylidene-1,1-bisphosphonic acid and pivaloyloxymethyl chloride in DMF in the presence of diisopropylethyl amine gives the tetra(pivaloyloxymethyl) ester of 1-hydroxyethylidene-bisphosphonic acid which is isolated as described in Example 4A.

S. Preparation of 4-Benzyloxycarbonylamino-1-hydroxybutylidene-1,1-bisphosphonic Acid Tri(2,2-dimethylbutanoyloxymethyl) Ester Following the procedure of 2A, the title compound was prepared by the reaction of 4-benzyloxycarbonylamino-1-hydroxybutylidene-1,1-bisphosphonic acid and chloromethyl 2,2-dimethylbutyrate in DMF in the presence of diisopropylethylamine followed by isolation as described.

$^1$H-NMR($CDCl_3$): δ 0.81 (t, 9H), 1.17 (s, 18H), 1.58 (q, 6H), 1.80 (brs, 2H), 2.0 (brs, 2H), 3.20 (m, 2H), 5.09 (s, 2H), 5.70 (m, 6H), 7.32 (m, 5H).

T. Preparation of Methylene-bisphosphonic Acid Tetra(pivaloyloxymethyl) Ester

A solution of methylene-bisphosphonic acid (1.0 g, 5.68 mmol), diisopropylethyl amine (6.0 ml, 34.4 mmol) and pivaloyloxymethyl chloride (5.0 ml, 40.4 mmol) in DMF (100 ml) was stirred at 80° C. for 8 hours. After concentrating under reduced pressure at 50° C., the residue was partitioned between brine and ethyl acetate. the organic extract was washed with brine, dried ($Na_2SO_4$), filtered and concentrated to give 2.4 g (69%) of the title compound.

$^1$H-NMR (300 MHz, $CDCl_3$): δ 1.2 (m, 36H), 2.55 (t, 2H), 5.68 (m, 8H).

U. Preparation of [(4-Chlorophenyl)thio]methylenebisphosphonic Acid Tetra(pivaloyloxymethyl) Ester Substitution of [(4-chlorophenyl)thio]methylene-bisphosphonic acid for methylene-bisphosphonic acid of Example 2T gives the tetra(pivaloyloxymethyl)ester of [(4-chlorophenyl)thio]methylene-bisphosphonic acid.

EXAMPLE 3

Deprotection of protected amino hydroxybisphosphonate esters

A. Preparation of 4-Amino-1-hydroxybutylidene-1,1-bisphosphonic Acid Tri(pivaloyloxymethyl) Ester A solution of 4-benzyloxycarbonylamino-1-hydroxybutylidene-1,1-bisphosphonic acid tri(pivaloyloxymethyl) ester (123 mg, 0.17 mmol) in absolute EtOH (40 ml) was hydrogenated over a 5% Pd/C catalyst (300 mg) at 42 psi of hydrogen for 2 hours. After filtering through diatomaceous earth and concentrating under reduced pressure, the residue was dissolved in water containing a little acetonitrile and lyophilized to give 70 mg (70%) of analytically pure 4-amino-1-hydroxybutylidene-1,1-bisphosphonic acid tri(pivaloyloxymethyl) ester.

Anal. Calcd. for $C_{22}H_{43}NO_{13}P_2$: C, 44.67; H, 7.33; N, 2.37; Found: C, 44.88; H, 7.01; N, 2.16.

B. Preparation of 4-Amino-1-hydroxybutylidene-1,1-bisphosphonic Acid Tri(pivaloyloxymethyl) Ester (Alternate method)

4-Benzyloxycarbonylamino-1-hydroxbutylidene-1,1-bisphosphonic acid tri(pivaloyloxymethyl) ester (5.9 g, 0.008 moles) was dissolved in 200 ml of methanol and hydrogenated over 2 grams of 5% palladium on carbon at 40 psi and 25° C. for two hours.

The catalyst was removed by filtration and the methanol was removed by concentrating under reduced pressure at 25° C. The product was dissolved in 192 ml of dry isopropyl acetate, deionized water, (1.9 ml) was added and the solution was stirred for 18 hours. The resulting crystals were collected by filtration and washed with isopropyl acetate. The isolated yield was 86%.

Anal. Calcd. for $C_{22}H_{43}NO_{13}P_2 \cdot H_2O$: C, 43.35; H, 7.39; N, 2.30; Found: C, 43.70; H, 7.28; N, 2.22.

$^{31}$P-NMR(CD$_3$OD)(H$_3$PO$_4$ reference): $\delta$ 10.1–10.5 (d, J=35 Hz), 21.5–21.8 (d, J=35 Hz).

C. Preparation of 4-Amino-1-hydroxybutylidene-1,1-bisphosphonic Acid Di(pivaloyloxymethyl) Ester A solution of 4-benzyloxycarbonylamino-1-hydroxybutylidene-1,1-bisphosphonic acid di(pivaloyloxymethyl) ester (65 mg) in absolute EtOH (50 ml) was hydrogenated over a 5% Pd/C catalyst (200 mg) at 30 psi of hydrogen for 2.5 hours. After filtering through diatomaceous earth and concentrating under reduced pressure, the residue was dissolved in water containing a little acetonitrile and lyophilized to give 18 mg (35%) of 4-amino-1-hydroxybutylidene-1,1-bisphosphonic acid di(pivaloyloxymethyl) ester.

Anal. Calcd. for $C_{16}H_{33}NO_{11}P_2 \cdot 2H_2O$: C, 34.59; H, 6.85; N, 2.52; Found: C, 34.17; H, 6.70; N, 2.33.

$^{31}$P-NMR(CD$_3$OD)(H$_3$PO$_4$ reference): $\delta$ 16.0 (s).

D. Preparation of 4-Amino-1-hydroxybutylidene-1,1-bisphosphonic Acid Di(pivaloyloxymethyl) Ester monosodium salt 4-Benzyloxycarbonylamino-1-hydroxybutylidene-1,1-bisphosphonic acid di(pivaloyloxymethyl) ester monosodium salt (2.27 g, 0.005 mol) was hydrogenated by the procedure of Example 3B. After removal of the catalyst by filtration, the catalyst was washed with 100 ml of water. The filtrate was concentrated to an oil and 30 ml of MeOH were added. The product, which crystallized within a few minutes, was collected by filtration and dried to give 1.54 g of the title compound.

Anal. Calcd. for $C_{16}H_{32}NO_{11}P_2Na \cdot 2H_2O$: C, 35.3; H, 6.8; N, 2.57; Found: C, 35.1; H, 6.6; N, 2.53; (corrected for water of hydration).

E. Preparation of 4-Amino-1-hydroxybutylidene-1,1-bisphosphonic Acid Tri[(2-ethyl)butanoyloxymethyl] Ester 4-Benzyloxycarbonylamino-1-hydroxybutylidene-1,1-bisphosphonic acid tri[(2-ethyl)butanoyloxymethyl] ester monosodium salt (974 mg) was hydrogenated by the procedure of Example 3B to give 600 mg of the title compound.

Anal. Calcd. for $C_{25}H_{46}NO_{13}P_2$: C, 47.39; H, 7.74; N, 2.21; Found: C, 47.64; H, 7.65; N, 2.07.

$^{31}$P-NMR(CD$_3$OD)(H$_3$PO$_4$ reference): $\delta$ 10.0–10.3 (d, J=35 Hz), 21.4–21.8 (d, J=35 Hz).

F. Preparation of 4-Amino-1-hydroxybutylidene-1,1-bisphosphonic Acid Di[(2-ethyl)butanoyloxymethyl] Ester 4-Benzyloxycarbonylamino-1-hydroxybutylidene-1,1-bisphosphonic acid di[(2-ethyl)butanoyloxymethyl] ester was hydrogenated by the procedure of Example 3B to give the title compound.

Anal. Calcd. for $C_{18}H_{27}NO_{11}P_2 \cdot H_2O$: C, 41.30; H, 7.46; N, 2.68; Found: C, 41.81; H, 7.21; N, 2.70.

$^{31}$P-NMR(CD$_3$OD)(H$_3$PO$_4$ reference): $\delta$ 16.1 (s)

G. Preparation of N-Methyl-4-amino-1-hydroxybutylidene-1,1-bisphosphonic Acid Tri(pivaloyloxymethyl) Ester N-Methyl-4-benzyloxycarbonylamino-1-hydroxybutylidene-1,1-bisphosphonic acid tri(pivaloyloxymethyl) ester (600 mg) was hydrogenated by the procedure of Example 3B to give 150 mg of the title compound.

Anal. Calcd. for $C_{23}H_{45}NO_{13}P_2$: C, 45.62; H, 7.49; N, 2.31; Found: C, 44.88; H, 7.65; N, 2.15.

$^{31}$P-NMR(CD$_3$OD)(H$_3$PO$_4$ reference): $\delta$ 10.0–10.4 (d, J=35 Hz), 21.4–21.7 (d, J=35 Hz).

H. Preparation of N-Methyl-4-amino-1-hydroxybutylidene-1,1-bisphosphonic Acid Di(pivaloyloxymethyl) Ester N-Methyl-4-benzyloxycarbonylamino-1-hydroxybutylidene-1,1-bisphosphonic acid di(pivaloyloxymethyl) ester (190 mg) was hydrogenated by the procedure of Example 3B to give 80 mg of the title compound.

Anal. Calcd. for $C_{17}H_{35}NO_{11}P_2 \cdot 4H_2O$: C, 34.85; H, 7.17; N, 2.39; Found: C, 35.13; H, 6.18; N, 2.16.

$^{31}$P-NMR(CD$_3$OD)(H$_3$PO$_4$ reference): $\delta$ 15.9 (s).

I. Preparation of N-Methyl-4-amino-1-hydroxybutylidene-1,1-bisphosphonic Acid Tri[(2-ethyl)butanoyloxymethyl] Ester N-Methyl-4-benzyloxycarbonylamino-1-hydroxybutylidene-1,1-bisphosphonic acid tri[2-ethyl)butanoyloxymethyl) ester was hydrogenated by the procedure of Example 3B to give the title compound.

Anal. Calcd. for $C_{27}H_{54}NO_{13}P_2 \cdot H_2O$: C, 46.87; H, 7.96; N, 2.10; Found: C, 46.94; H, 7.35; N, 2.26.

$^{31}$P-NMR(CD$_3$OD)(H$_3$PO$_4$ reference): $\delta$ 10.2–10.5 (d, J=35 Hz), 21.6–22.0 (d, J=35 Hz).

J. Preparation of N-Methyl-4-amino-1-hydroxybutylidene-1,1-bisphosphonic Acid Di[(2-ethyl)butryloxymethyl] Ester N-Methyl-4-benzyloxycarbonylamino-1-hydroxybutylidene-1,1-bisphosphonic acid di[(2-ethyl)butryloxymethyl] ester was hydrogenated by the procedure of Example 3B to give the title compound.

Anal. Calcd. for $C_{19}H_{39}NO_{11}P_2\cdot H_2O$: C, 41.08; H, 7.39; N, 2.52; Found: C, 41.31; H, 7.05; N, 2.58.

$^{31}P$-NMR($CD_3OD$)($H_3PO_4$ reference): $\delta$ 16.0 (s).

K. Preparation of 4-Amino-1-hydroxybutylidene-1,1-bisphosphonic Acid Tri(isobutanoyloxymethyl) Ester Removal of the amino protective group from 3-benzyloxycarbonylamino-1-hydroxybutylidene-1,1-bisphosphonic acid tri(isobutanoyloxymethyl) ester by the procedure of Example 3A gives the tri(isobutanoyloxymethyl) ester of 4-amino-1-hydroxybutylidene-1,1-bisphosphonic acid.

L. Preparation of 4-Amino-1-hydroxybutylidene-1,1-bisphosphonic Acid Tri(2-ethylbutanoyloxymethyl) Ester Removal of the amino protective group from 4-benzyloxycarbonylamino-1-hydroxybutylidene-1,1-bisphosphonic acid tri(2-ethylbutanoyloxymethyl) ester by the procedure of Example 3A yielded the tri(2-ethylbutanoyloxymethyl) ester of 4-amino-1-hydroxybutylidene-1,1-bisphosphonic acid. Anal. Calcd, For $C_{25}H_{49}NO_{13}P_2$: C, 47.39; H, 7.74; N, 2.21; Found: C, 47.64; H, 7.65; N, 2.07.

M. Preparation of 3-Amino-1-hydroxypropylidene-1,1-bisphosphonic Acid Tri(pivaloyloxymethyl) Ester Removal of the amino protective group from 3-benzyloxycarbonylamino-1-hydroxy-propylidene-1,1-bisphosphonic acid tri(pivaloyloxymethyl) ester by the procedure of Example 3A gives the tri(pivaloyloxymethyl) ester of 3-amino-1-hydroxypropylidene-1,1-bisphosphonic acid.

N. Preparation of 4-(1-hydroxymethylene-1,1-bisphosphonic acid)piperidine tri(pivaloyloxymethyl) Ester Removal of the amino protective group from N-benzyloxycarbonyl-4-(1-hydroxymethylene-1,1-bisphosphonic acid)piperidine tri(pivaloyloxymethyl) ester by the procedure of Example 3A gives the tri(pivaloyloxymethyl) ester of 4-(1-hydroxymethylene-1,1-bisphosphonic acid)piperidine.

O. Preparation of 4-Amino-1-hydroxybutylidene-1,1-bisphosphonic Acid Tri(2,2-dimethylbutanoyloxymethyl) Ester Removal of the amino protective group from 4-benzyloxycarbonylamino-1-hydroxybutylidene-1,1-bisphosphonic acid tri(2,2-dimethylbutanoyloxymethyl) ester by the procedure of Example 3A gave the title compound.

Anal. Calcd, For $C_{25}H_{49}NO_{13}P_2\cdot H_2O$: C, 46.08; H, 7.89; N, 2.15; Found: C, 46.36; H, 7.64; N, 2.08

$^{1}H$-NMR(DMSO-$d_6$): $\delta$0.80 (t, 9H), 1.12 (s, 18H), 1.54 (m, 6H), 1.88 (brs, 4H), 2.76 (brs, 2H), 5.55 (m, 6H).

EXAMPLE 4

Preparation of halo-bisphosphonates

A. Preparation of Dichloromethylene-bisphosphonic Acid Tetra(pivaloyloxymethyl) Ester A 5.25% solution of sodium hypochlorite in water (4.4 ml, 3.4 mmol) was added dropwise over 10 minutes to a stirred solution of methylenebisphosphonic acid tetra(pivaloyloxymethyl) ester (1.0 g, 1.58 mmol) in $CHCl_3$ (5 ml). After addition was complete, the reaction mixture was stirred at room temperature for 1 hour and then allowed to stand overnight. Additional $CHCl_3$ was added and the aqueous layer separated. After drying ($Na_2SO_4$) and filtering the solvent was removed under reduced pressure to give the tetra(pivaloyloxymethyl)ester of dichloro-methylene-bisphosphonic acid.

$^{1}H$-NMR (300 MHz, $CDCl_3$): $\delta$1.18 (m, 36H), 5.65 (m, 8H).

Effect in Preventing Bone Loss Associated with Immobilization—Oral Study

Groups of male Sprague-Dawley derived rats weighing about 250 grams were given the test compound (in citrate buffer) by oral administration in one dose of either 0.5 mg P/kg, 1.0 mg P/kg or 2.0 mg P/kg each for 4-amino-1-hydroxybutylidene-1,1-bisphosphonic acid di(pivaloyloxymethyl) ester [ABPdi(POM)] on day −2 before surgery, and in one dose again on day −1 before surgery (dosages are expressed as mg ABP per kg body weight of the subject). On day 0 all rats underwent surgery whereby the sciatic nerve of the right hind limb was severed. Ten days following immobilization surgery, the rats were sacrificed and hind limbs removed. The femora were defleshed, maximum femoral length of both femora measured and then placed in a muffle furnace at 700° C. for 24 hours. Ash weight was then determined and the data are reported in Table 1. As indicated in Table 1, 4-amino-1-hydroxybutylidene-1,1-bisphosphonic acid di(pivaloyloxymethyl) ester was effective at reducing bone loss upon oral administration.

TABLE 1

| Compound | Dose (mg P/kg) | n | mg Diff | se |
|---|---|---|---|---|
| ABPdi(POM) | 0.5 | 4 | 25.0 | 2.7 |
| | 1.0 | 4 | 18.4 | 3.5 |
| | 2.0 | 4 | 15.0 | 0.9 |
| Vehicle (citrate buffer) | 0 | 5 | 35.0 | 4.6 | n = animals/group
mg Diff = difference in ash weight between the intact femur and the immobilized femur
se = standard error of the mean.

Effect in Preventing Bone Loss Associated with Immobilization—Subcutaneous Study Groups of male Sprague-Dawley derived rats weighing about 250 grams were given the test compound, (as a solution in citrate buffer) by subcutaneous administration in one dose of either 0.1 mg P/kg, 0.5 mg P/kg or 1.0 mg P/kg each for 4-amino-1-hydroxybutylidene-1,1-bisphosphonic acid di(pivaloyloxymethyl) ester [ABPdi(POM)] and 4-amino-1-hydroxybutylidene-1,1-bisphosphonic acid tri(pivaloyloxymethyl) ester [ABPtri(POM)] each on day −2 before surgery, and in one dose again on day −1 before surgery to produce immobilization (dosages are expressed as mg ABP per kg body weight of the subject). Immobilization was produced by unilateral hind limb sciatic neurectomy. Ten days after surgery the rats were sacrificed, hind limbs removed, and the femora ashed at 700° C. for 24 hours. Ash weight was determined and the difference between the ash weight of the intact limb and immobilized limb was calculated and expressed as the mg difference. As indicated in Table 2, 4-amino-1-hydroxybutylidene-1,1-bisphosphonic acid di(pivaloyloxymethyl) ester and 4-amino-1-hydroxybutylidene-1,1-bisphosphonic acid tri(pivaloyloxymethyl) ester were effective at reducing bone loss upon subcutaneous administration.

TABLE 2

| Compound | Dose (mg P/kg) | n | mg Diff | se |
|---|---|---|---|---|
| ABPdi(POM) | 0.1 | 4 | 15.4 | 2.3 |
|  | 0.5 | 4 | 7.3 | 2.8 |
|  | 1.0 | 4 | 11.1 | 2.3 |
| ABPtri(POM) | 0.1 | 4 | 24.0 | 1.0 |
|  | 0.5 | 4 | 15.8 | 1.6 |
|  | 1.0 | 4 | 14.0 | 1.4 |
| Vehicle (citrate buffer) | 0 | 6 | 27.6 | 0.5 | n = animals/group
mg Diff = difference in ash weight between the intact femur and the immobilized femur
se = standard error of the mean.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the formula:

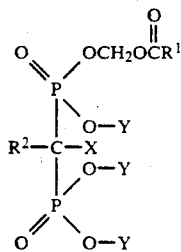

or a pharmaceutically acceptable salt thereof, wherein:
$R^1$ is independently, $C_{1-12}$alkyl;
$R^2$ is
  1) $C_{1-10}$alkyl, either unsubstituted or substituted with
    a) $-NR^3R^4$, wherein R3 and R4 are the same or different and are
      i) hydrogen,
      ii) $C_{1-6}$alkyl, or
      iii) joined together directly to form a 5-7 membered ring selected from pyrrolidino, or through a heteroatom selected from O and N, to form a 6-membered heterocycle selected from morpholino, piperazino, and N-$C_{1-3}$alkyl-piperazino with the nitrogen to which they are attached,
    b) $-OH$,
    c) halo,
    d) $-S(C_{1-6}alkyl)$,
    e) phenyl,
    f) $C_{1-7}$cycloalkyl, either unsubstituted or substituted with
      i) $-NR^3R^4$,
      ii) $-OH$, or
    g) pyridyl;
  2) $C_{3-7}$cycloalkyl, either unsubstituted or substituted with
    a) $-NR^3R^4$,
    b) $-OH$,
    c) halo,
    d) $-S(C_{1-6}alkyl)$,
    e) phenyl,
    f) morpholino, or
    g) pyridyl;
  3) halo;
  4) pyrrolidinyl;
  5) $-S-(C_{1-6}alkyl)$, either unsubstituted or substituted with
    a) $-NR^3R^4$,
    b) $-OH$,
    c) halo, or
    d) phenyl,
  6) $-S-$phenyl wherein the phenyl may be unsubstituted or substituted with
    a) halo,
    a) nitro,
    c) $C_{1-6}$alkyl,
    d) $C_{1-C_6}$ alkoxy,
    e) trifluoromethyl,
    f) $-CONR^3R^4$, or
    g) $-COOH$;
Y is independently, hydrogen or

wherein $R^1$ is as defined above; and
X is hydrogen, halo or hydroxyl.

2. The compound of claim 1 wherein:
$R^1$ is $C_1$-$C_{12}$ alkyl;
$R^2$ is
  1) $C_{1-6}$alkyl, either unsubstituted or substituted with
    a) $-NR^3R^4$, wherein R3 and R4 are the same or different and are hydrogen or $C_{1-6}$alkyl,
    b) morpholino, or
    c) pyridyl;
  2) pyrrolidinyl; and
X is hydroxyl.

3. The compound of claim 1 wherein:
$R^1$ is tert-butyl, isobutyl, 2-ethylbutyl or 2,2-dimethylbutyl;
$R^2$ is $C_{1-3}$alkyl substituted with $-NR^3R^4$, wherein R3 and R4 are the same or different and are hydrogen or $C_{1-6}$alkyl; and
X is hydroxyl.

4. A pharmaceutical composition for treating diseases involving bone resorption which comprises a therapeutically effective amount of a compound of claim 1 and a pharmaceutically acceptable carrier.

5. A pharmaceutical composition for treating diseases involving bone resorption which comprises a therapeutically effective amount of a compound of claim 2 and a pharmaceutically acceptable carrier.

6. A method for treating diseases involving bone resorption which comprises administering to a patient, in need of such treatment, a nontoxic therapeutically effective amount of a compound of claim 1.

7. A method for treating diseases involving bone resorption which comprises administering to a patient, in need of such treatment, a nontoxic therapeutically effective amount of a compound of claim 2.

8. The method of claim 6, which comprises orally administering the compound in an amount of 0.5 µg to 5 mg per kilogram bodyweight per day.

9. The method of claim 7, which comprises orally administering the compound in an amount of 0.5 µg to 5 mg per kilogram bodyweight per day.

10. The method of claim 6, which comprises parenterally administering the compound in an amount of 0.5 µg to 5 mg per kilogram bodyweight per day.

11. A method for the prophylactic treatment of postmenopausal osteoporosis which comprises administering an effective amount of a compound of claim 1.

12. The method of claim 11 wherein said compound is administered in an amount of 1 µg to 1 mg per kilogram bodyweight per day.

13. A compound which is selected from the group consisting of:
4-amino-1-hydroxybutylidene-1,1-bisphosphonic acid mono(pivaloyloxymethyl) ester;
4-amino-1-hydroxybutylidene-1,1-bisphosphonic acid di(pivaloyloxymethyl) ester;
4-amino-1-hydroxybutylidene-1,1-bisphosphonic acid tri(pivaloyloxymethyl) ester;
4-amino-1-hydroxybutylidene-1,1-bisphosphonic acid tetra(pivaloyloxymethyl) ester;
4-amino-1-hydroxybutylidene-1,1-bisphosphonic acid di(pivaloyloxymethyl) ester monosodium salt;
4-amino-1-hydroxybutylidene-1,1-bisphosphonic acid di[(2-ethyl)butanoyloxymethyl] ester;
4-amino-1-hydroxybutylidene-1,1-bisphosphonic acid tri[(2-ethyl)butanoyloxymethyl] ester;
4-amino-1-hydroxybutylidene-1,1-bisphosphonic acid tri(2,2-dimethylbutanoyloxymethyl) ester; and
4-amino-1-hydroxybutylidene-1,1-bisphosphonic acid tri(isobutanoyloxymethyl) ester.

14. A compound which is selected from the group consisting of:
N-methyl-4-amino-1-hydroxybutylidene-1,1-bisphosphonic acid di(pivaloyloxymethyl) ester;
N-methyl-4-amino-1-hydroxybutylidene-1,1-bisphosphonic acid tri(pivaloyloxymethyl) ester;
N-methyl-4-amino-1-hydroxybutylidene-1,1-bisphosphonic acid di[(2-ethyl)butanoyloxymethyl], ester;
N-methyl-4-amino-1-hydroxybutylidene-1,1-bisphosphonic acid tri[(2-ethyl)butanoyloxymethyl] ester;
4-(N,N-dimethylamino)-1-hydroxybutylidene-1,1-bisphosphonic acid tri(pivaloyloxymethyl) ester;
3-amino-1-hydroxypropylidene-1,1-bisphosphonic acid tri(pivaloyloxymethyl) ester;
3-(N,N-dimethylamino)-1-hydroxypropylidene-1,1-bisphosphonic acid tri(pivaloyloxymethyl) ester;
1-hydroxy-3-(N-methyl-N-pentylamino)propylidene-1,1-bisphosphonic acid tri(pivaloyloxymethyl) ester;
1-hydroxy-2-[3-pyridyl]ethylidene-bisphosphonic acid tri(pivaloyloxymethyl) ester; and
4-(hydroxymethylene-bisphosphonic acid)piperidine tri(pivaloyloxymethyl) ester.

15. A compound which is selected from the group consisting of:
1-hydroxyethylidene-1,1-bisphosphonic acid tri(pivaloyloxymethyl) ester;
1-hydroxyethylidene-1,1-bisphosphonic acid tetra(pivaloyloxymethyl) ester;
[(4-chlorophenyl)thio]methylene-bisphosphonic acid tri(pivaloyloxymethyl) ester;
[(4-chlorophenyl)thio]methylene-bisphosphonic acid tetra(pivaloyloxymethyl) ester;
dichloromethylene-bisphosphonic acid tetra(pivaloyloxymethyl) ester;
difluoromethylene-bisphosphonic acid tetra(pivaloyloxymethyl) ester; and
methylene-bisphosphonic acid tetra(pivaloyloxymethyl) ester.

16. A pharmaceutical composition for treating diseases involving bone resorption which comprises a therapeutically effective amount of the compound of claim 13 and a pharmaceutically acceptable carrier.

17. A pharmaceutical composition for treating diseases involving bone resorption which comprises a therapeutically effective amount of the compound of claim 14 and a pharmaceutically acceptable carrier.

18. A pharmaceutical composition for treating diseases involving bone resorption which comprises a therapeutically effective amount of the compound of claim 15 and a pharmaceutically acceptable carrier.

19. A method for treating diseases involving bone resorption which comprises administering to a patient, in need of such treatment, a nontoxic therapeutically effective amount of the compound of claim 13.

20. A method for treating diseases involving bone resorption which comprises administering to a patient, in need of such treatment, a nontoxic therapeutically effective amount of the compound of claim 14.

21. A method for treating diseases involving bone resorption which comprises administering to a patient, in need of such treatment, a nontoxic therapeutically effective amount of the compound of claim 15.

* * * * *